United States Patent [19]

Keyes et al.

[11] Patent Number: 4,700,872
[45] Date of Patent: Oct. 20, 1987

[54] DISPENSING PUMP FOR SYRINGE

[76] Inventors: Paul H. Keyes, 5716 Tanglewood Dr., Bethesda, Md. 20817; Marvin J. Taves, N-414, 1301 Delaware Ave., SW., Washington, D.C. 20024

[21] Appl. No.: 897,928

[22] Filed: Aug. 19, 1986

[51] Int. Cl.$^4$ .......................... B65D 83/00; A61M 5/18
[52] U.S. Cl. .................................... 222/162; 222/399; 222/401; 604/184
[58] Field of Search ............................... 604/124–125, 604/181, 183–184, 186, 203, 231; 417/545, 548, 550–552; 222/162, 183, 204, 372, 377, 380–384, 398–399, 401, 402; 239/320–322, 331, 333, 373

[56] References Cited

U.S. PATENT DOCUMENTS

| 1,563,627 | 12/1925 | Hein | 604/231 X |
| 2,743,847 | 5/1956 | Pollak | 222/383 X |
| 2,880,939 | 4/1959 | Esmay | 239/320 X |
| 3,191,807 | 6/1965 | Rodrigues, Jr. | 222/380 X |
| 4,036,232 | 7/1977 | Genese | 604/250 X |
| 4,175,704 | 11/1979 | Cohen | 239/320 |
| 4,537,334 | 8/1985 | Spengler et al. | 222/401 |

FOREIGN PATENT DOCUMENTS 2029179 4/1972 Fed. Rep. of Germany ...... 604/184

Primary Examiner—Joseph J. Rolla
Assistant Examiner—Michael S. Huppert
Attorney, Agent, or Firm—Nies, Webner, Kurz & Bergert

[57] ABSTRACT

A pump for dispensing liquid via a syringe has a chamber in which a hollow cylinder is mounted. The cylinder is connected to the chamber via a first normally closed check valve. A hollow plunger reciprocates in the cylinder is connected thereto via a second normally closed check valve. A charge of liquid is placed in the hollow plunger. On the out-stroke of the piston, the liquid in the piston is sucked through the second normally closed check valve into the cylinder and on the in-stroke of the plunger the liquid is forced through the first normally closed check valve into the chamber wherein it is maintained under pressure created by the pumping action of the plunger. An outlet tube leads from the lower part of the chamber to a syringe and an normally closed pinch valve in the syringe is manually operable to permit liquid under pressure to be squirted from the syringe.

3 Claims, 1 Drawing Figure

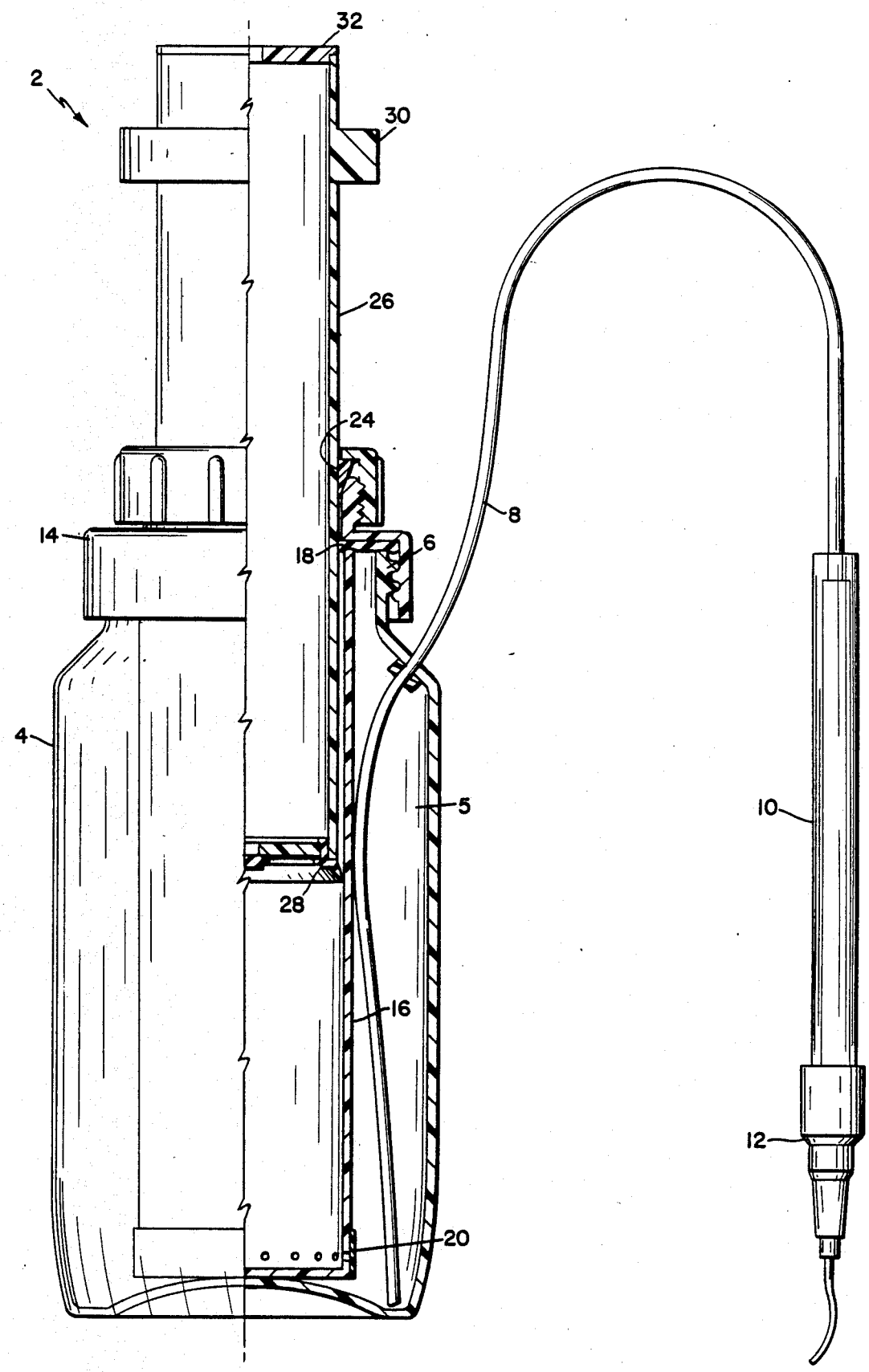

DISPENSING PUMP FOR SYRINGE

FIELD OF INVENTION

Class 222, subclass 162.

OBJECTS

The primary object of this invention is to provide a pump device that will enable the user to deliver medicated solutions with precision through a syringe-type tip into some of the more inaccessible parts of the human body or into such parts in the bodies of animals. Although this device has been designed especially as an aid for oral hygiene that will enable patients to carefully control the introduction of medicaments into interdental spaces, gingival crevices, periodontal pockets, and dental furcations, it may also be used for the delivery of medicaments to other parts of the human body, e.g., the nostrils, external auditory meatuses, infected wounds, fistullae, etc. The device may be used by dentists in the treatment of patients, for example in the treatment of infected pulp canals, in the irrigation of periodontal pockets, in the debridement of tooth sockets after surgery, or in the treatment of "dry sockets" and infected tissues around partially erupted third molars. Physicians and nurses may also find the device helpful in the treatment of infected wounds, etc.

The pump is convenient to use, as it can be filled without removing the piston from the chamber. Furthermore, two or more different liquids can be mixed and monitored visually during the filling operation. This eliminates the need for intermediate vessels. The pump does not inactivate solutions such as hydrogen peroxide, as is the case with devices that use pulsating pumping systems to deliver solutions.

A more specific object is to provide a dispensing pump having a container enclosing a chamber in which a hollow cylinder is disposed, and a hollow piston reciprocatable in the cylinder, there being one check valve connecting the hollow piston and the cylinder and another check valve connecting the hollow cylinder and the chamber so that, on an out-stroke of the hollow piston a charge of liquid contained therein is sucked into the hollow cylinder past the first check valve and on the in-stroke of the piston the liquid in the cylinder is forced past the second check valve into the chamber, where it remains under pressure until dispensed by a valve-controlled syringe connected to the chamber via a flexible outlet tube.

A further object is to provide, in connection with the foregoing pump, wherein a charge of liquid is maintained under pressure in a chamber and a syringe connected to the chamber via a flexible outlet tube has a normally closed valve therein whereby the operator, by opening the valve, may squirt out the liquid contained in the pump chamber in short or long bursts, as he desires, by opening the valve.

Still another object is to provide a dispensing pump for a syringe comprised of only a few simple parts which may easily be dis-assembled for cleaning, and which preferably is made of clear, flexible plastics so that the liquid contained in the pump chamber may easily be seen and the amount judged.

BRIEF DESCRIPTION OF THE DRAWING

These and other objects will be apparent in the following specification and drawing in which the sole FIGURE is a side elevation, partly broken away, showing the pump and the cylinder, piston and check valves therein, and the syringe.

Referring now to the drawing, the dispensing pump 2 is disposed in the container 4 enclosing a chamber 5, which container has a threaded neck 6 and a flexible outlet tube 8 leading from the lower part of the chamber to a syringe 10 having a manually operated normally closed pinch valve 12. An apertured cap 14 screwed onto the threaded neck of container 4 supports a hollow cylinder 16 mounted on and extending through the cap and sealed to the container neck by gasket 18. In the bottom of hollow cylinder 16 is a normally closed check valve 20 which permits liquid to flow out of the cylinder into the chamber 5, but which blocks flow of liquid back from the chamber 5 to the interior of the cylinder 16. A ring 24 attached to apertured cap 14 slideably supports a hollow piston 26 having a check valve 28 on its lower end which permits liquid to flow from hollow piston 26 into hollow cylinder 16, but which blocks reverse flow from the cylinder 16 into the hollow piston 26. A flange 30 adjacent the upper end of the hollow piston limits the movement of the piston into the cylinder and a removable vented lid 32 on the outer end piston 26 is provided.

In operation, let it be assumed that hollow piston 26 has been stroked inwardly and a charge of liquid to be dispensed is filled into the hollow piston. When piston 26 is pulled outwardly, the liquid charge therein is sucked past check valve 28 on the lower end of the piston into hollow cylinder 16. and on the in-stroke of the piston the liquid which has been sucked into hollow cylinder 16 is forced past the normally closed check valve 20 in the lower end of the cylinder. Assuming that the valve 12 on syringe 10 is closed, pressure is created in the chamber 5 and when the normally closed valve 12 is opened, a fine stream of liquid will be squirted out through the syringe.

We claim:

1. A pump for dispensing a charge of liquid comprising:
    a container defining a pump chamber,
    a hollow cylinder supported in said chamber, said cylinder having an inner end connecting with said chamber via a first normally closed check valve which opens towards the chamber and an open outer end directed outwardly of the chamber,
    a hollow plunger slideably disposed in said cylinder and connecting with the interior thereof via a second normally closed check valve opening towards the interior of the cylinder, said plunger having a normally open outer end adapted to receive a charge of liquid to be dispensed whereby upon out-stroke of the plunger, liquid is sucked through the second check valve from the plunger into the cylinder and upon in-stroke of the plunger the liquid is forced through the first check valve into the chamber,
    outlet conduit means for said chamber, and means for controlling the flow of liquid through said outlet conduit means.

2. A pump as claimed in claim 1, said outlet conduit means comprising a flexible, hollow tube having one end connecting with the interior of the chamber and an opposite end connected to one end of a syringe, the syringe being normally closed by normally closed manually operable valve, whereby upon reciprocation of the plunger, air pressure may be built up in the pump chamber so that upon opening of the normally closed valve a stream of liquid under pressure is dispensed via the syringe.

3. A pump as claimed in claim 2, said pump being adapted for normal disposition in which the cylinder terminates adjacent a lower end of the chamber and the first check valve is disposed in the lower end of the cylinder, said outlet conduit extending from a lower portion of the chamber through a wall thereof adjacent the upper end thereof whereby in the normal operation of the pump a liquid occupies the lower portion of the chamber and is dispensed therefrom by pressurized air in the chamber.

* * * * *